(12) United States Patent
Schwab et al.

(10) Patent No.: US 11,253,235 B1
(45) Date of Patent: Feb. 22, 2022

(54) URINE ANALYSIS COLLECTOR

(71) Applicant: ExtraAim, LLC, East Chatham, NY (US)

(72) Inventors: Brian Schwab, East Chatham, NY (US); Cheng-Yang Lai, Taipei District (TW)

(73) Assignee: UrynX LLC, East Chatham, NY (US)

( * ) Notice: Subject to any disclaimer, the term of this patent is extended or adjusted under 35 U.S.C. 154(b) by 0 days.

(21) Appl. No.: 17/067,792

(22) Filed: Oct. 12, 2020

(51) Int. Cl.
*A61B 10/00* (2006.01)

(52) U.S. Cl.
CPC ........ *A61B 10/007* (2013.01); *A61B 2560/04* (2013.01)

(58) Field of Classification Search
CPC .. A61B 10/007; A61B 10/0045; A61M 39/00; A61M 39/10; A61M 39/20; B01L 3/50; B01L 3/5021; B01L 3/5023; B01L 3/5029; B01L 3/5082
See application file for complete search history.

(56) References Cited

U.S. PATENT DOCUMENTS

| | | | | | |
|---|---|---|---|---|---|
| 5,268,148 | A | * | 12/1993 | Seymour | A61B 10/0051 422/401 |
| 5,830,154 | A | * | 11/1998 | Goldstein | A61B 10/0051 600/572 |
| 7,387,899 | B1 | * | 6/2008 | D'Angelo | A61B 10/0051 422/500 |
| 2003/0129738 | A1 | * | 7/2003 | Sorenson | A61B 10/02 435/287.1 |
| 2003/0168365 | A1 | * | 9/2003 | Kaern | A61B 50/30 206/364 |
| 2007/0166198 | A1 | * | 7/2007 | Sangha | B01L 99/00 422/400 |
| 2013/0209993 | A1 | * | 8/2013 | Aronowitz | G01N 1/10 435/5 |
| 2017/0143314 | A1 | * | 5/2017 | Green | A61B 10/007 |
| 2018/0153522 | A1 | * | 6/2018 | Terbrueggen | B01L 3/5029 |
| 2019/0234540 | A1 | * | 8/2019 | Marici | A61M 39/165 |
| 2020/0383664 | A1 | * | 12/2020 | Loudermilk | B01L 3/5029 |

\* cited by examiner

*Primary Examiner* — Daniel L Cerioni
*Assistant Examiner* — Raymond P Dulman
(74) *Attorney, Agent, or Firm* — Michael D. Eisenberg

(57) ABSTRACT

A kit for urine collection is disclosed. The kit comprises a clip; a collector device comprising a connector portion configured for receiving the clip, a holder portion configured for receiving a sponge; and a stopper portion; a tube configured to receive the collector device; and a cap configured to be inserted onto an open end of the tube and seal the tube and simultaneously receive an end of the collector device into a recess disposed inside the cap.

12 Claims, 18 Drawing Sheets

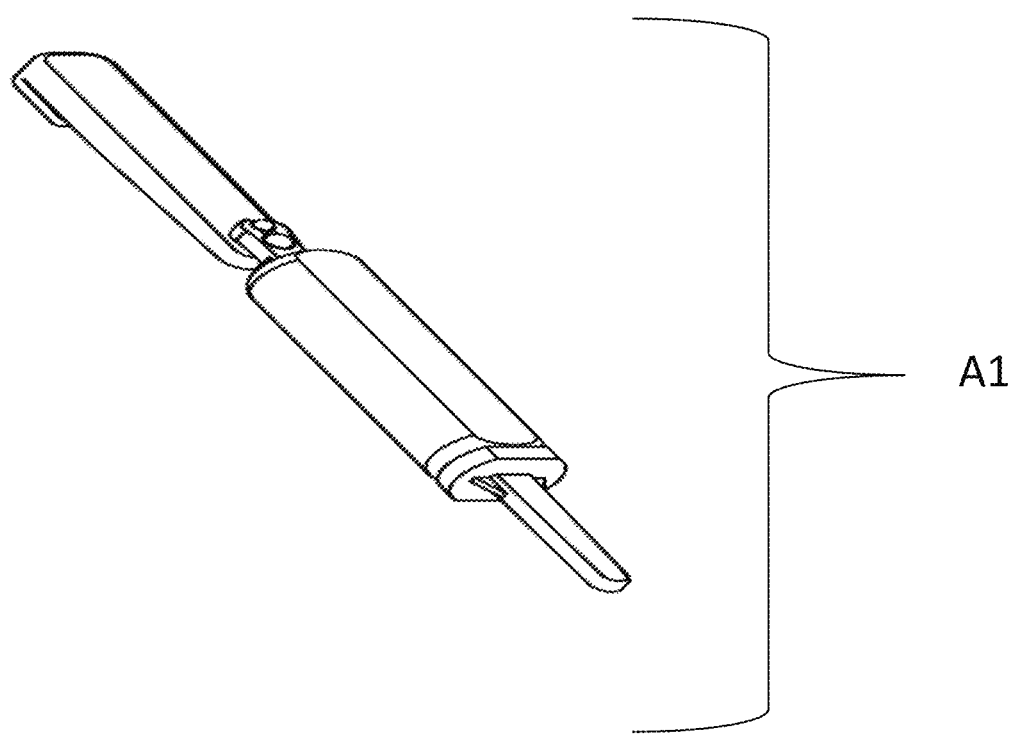
FIG. 1
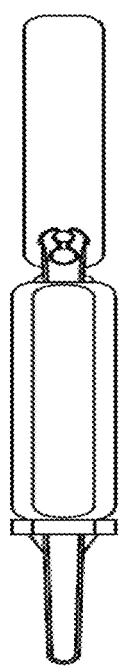    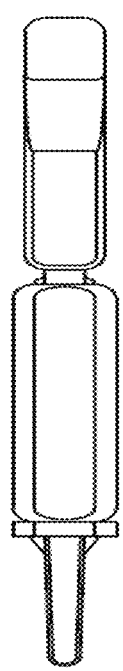    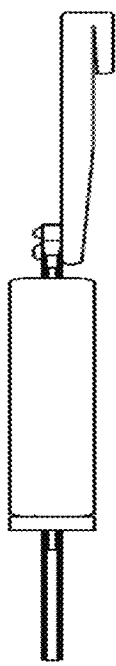
FIG. 2A            FIG. 2B            FIG. 2C

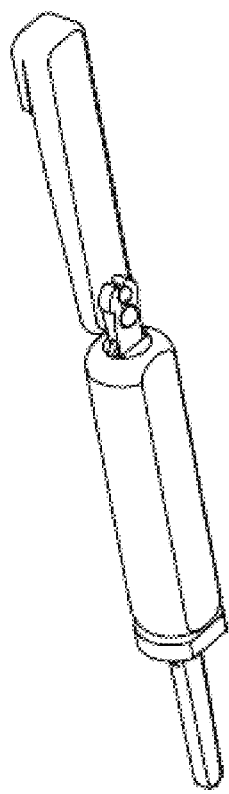
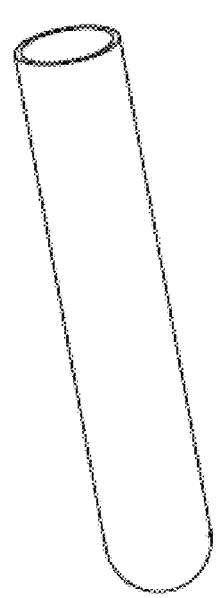
FIG. 4A
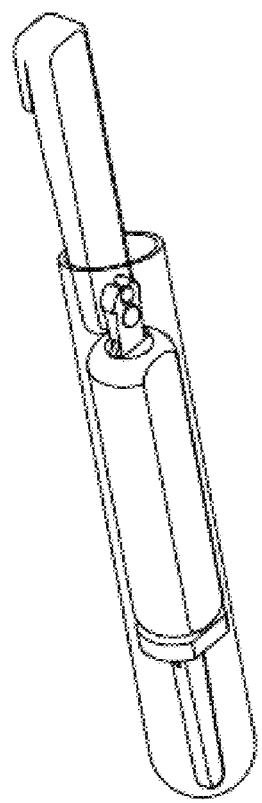
FIG. 4B

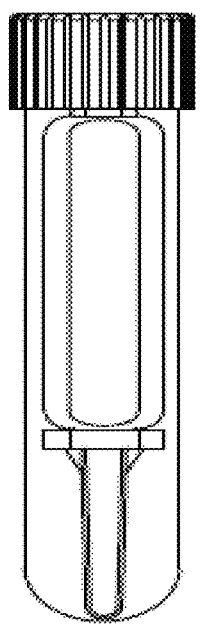
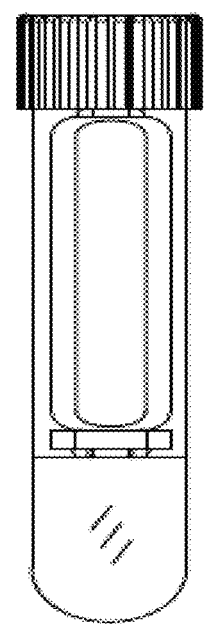
*FIG. 7A*  *FIG. 7B*
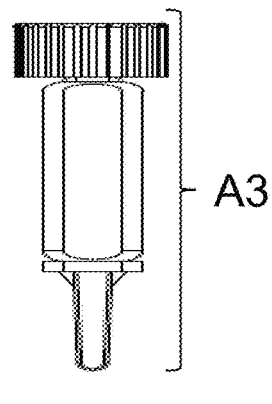
*FIG. 8*

URINE ANALYSIS COLLECTOR

BACKGROUND OF THE INVENTION

The spread of pandemics (COVID-19) and migration patterns where people are increasingly moving to exurban locations are factors which impose difficulties in obtaining biological samples or specimens for diagnostic testing. The contagiousness of COVID-19 has necessitated people to isolate from others. Diagnostic testing is needed which can use facilely obtained biological samples, while minimizing the risk of spreading pandemics (i.e., increasing safety when obtaining biological samples or specimens and efficiency for diagnostic testing). Exurban locations often lack the facilities for rapid, efficient, and safe diagnostic testing. Systems and methods are needed which enhance the efficiency of rapid and safe diagnostic testing for isolated populations.

SUMMARY OF THE EMBODIMENTS OF THE INVENTION

In a variant, a kit for urine collection comprises: a clip; a collector device comprising a connector portion configured for receiving the clip, a holder portion configured for receiving a sponge; and a stopper portion; a tube configured to receive the collector device; and a cap configured to be inserted onto an open end of the tube and seal the tube and simultaneously receive an end of the collector device into a recess disposed inside the cap.

In another variant, the kit further comprises a foil packet, wherein the foil packet comprises an air tight seal, a top portion configured for tearing, and material for resisting temperature changes, thereby protecting contents within the foil packets, wherein the contents comprise the clip, the collector device, the tube and the cap.

In a variant, a collector device comprises a connector portion configured for receiving a clip, wherein the connector comprises a first cavity and a second cavity; a holder portion configured for receiving a sponge, wherein the holder comprises a seat and a wall, thereby the sponge is disposed in between the seat and the wall; a stopper portion configured to contact a bottom surface of a tube; and a cap, wherein the cap is configured to seal the tube.

In another variant, the seat is operatively connected to a first knob and the wall is attached to a second knob.

In a further variant, the first cavity is operatively connected to the second cavity via a third cavity.

In a still another variant, the first cavity and the second cavity are receiving cavities and the third cavity is a pathway between the first cavity and the second cavity.

In yet a further variant, when the tube is spun in a centrifuge, urine is collected at the bottom surface of the tube.

In a variant, a collector device comprises: a connector portion configured for receiving a clip, wherein the connector comprises a first cavity and a second cavity; a holder portion configured for receiving a sponge, wherein the holder comprises a seat and a plurality of extenders, thereby the sponge is disposed in between the seat and the plurality of extenders; a stopper portion configured to contact a bottom surface of a tube and offset the holder portion away from the bottom of the tube; and a cap, wherein the cap is configured to seal the tube.

In another variant, the first cavity is operatively connected to the second cavity via a third cavity.

In a further variant, the first cavity and the second cavity are receiving cavities and the third cavity is a pathway between the first cavity and the second cavity.

In a still another variant, when the tube spun in a centrifuge, urine is collected at the bottom surface of the tube.

In yet another variant, the cap comprises a groove configured to receive an end of the connector, wherein when the device is placed in the tube, and the cap is sealed onto the tube, the connector is received into the groove of the cap into an assembly whereby the device may be removed from the tube by handling only the cap.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 1 is a depiction of a perspective view of the urine collection device attached with the clip.

FIG. 2A, FIG. 2B, and FIG. 2C are depictions of a front view, back view, and side view of the urine collection device, respectively.

FIG. 4A and FIG. 4B are depictions of the urine collection device with a clip placed into a centrifuge tube.

FIG. 7A is a depiction of the urine collection device in a sealed tube.

FIG. 7B is a depiction of urine extracted from the urine collection device in the sealed tube.

FIG. 8 is a depiction of a mechanism for removing the urine collection device from the sealed tube.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Reference is also made to the figures, as presented herein. The figures are not intended to be exhaustive or to limit the invention to the precise form disclosed. It should be understood that the invention can be practiced with modification and alteration, and that the invention be limited only by the claims and the equivalents thereof.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The systems and methods herein are directed to a urine analysis kit for telemedicine systems. The urine analysis kit comprises: one unit of a urine strip holder, two units of 10-parameter urine test strips in a foil packet, one unit of a urination device, one unit of a sterile zip-lock bag, and one unit of a sponge-mounted urine collection device.

The part number and corresponding description of the part are listed in Table 1.

TABLE 1

Components which construct the Urine Collection Device

| Sponge Stopper 105 | Sponge Holder 110A, 110B, 110C, or 110D | Connector 115 | Side extenders 120 |
| --- | --- | --- | --- |
| Receiving Cavity 125 | Receiving Cavity 127 | Receiving Cavity 130 | Wall 135 |
| Seat 140 | Support Extenders 145 | Sponge 150A, 150B, | Clip 155 |

TABLE 1-continued

Components which construct the Urine Collection Device

| | | 150C, or 150D | |
| --- | --- | --- | --- |
| Base 160 | Base 165 | Receiving Extender 170 | Receiving Extender 175 |
| Cap 180 | Extender 185 | Knob 190 | Support Extender 193 |
| Collection Device 195 (which comprises either sponge holder 110A, 110B, 110C, and 110D) | Clip 200 | Groove 205 | Groove 207 |
| Layer 209 | Layer 210 | Layer 211 | Layer 212 |
| Layer 213 | Cavity 215 | | |

To facilitate understanding the systems and methods herein, the following assemblies are listed below.

Figure 3:
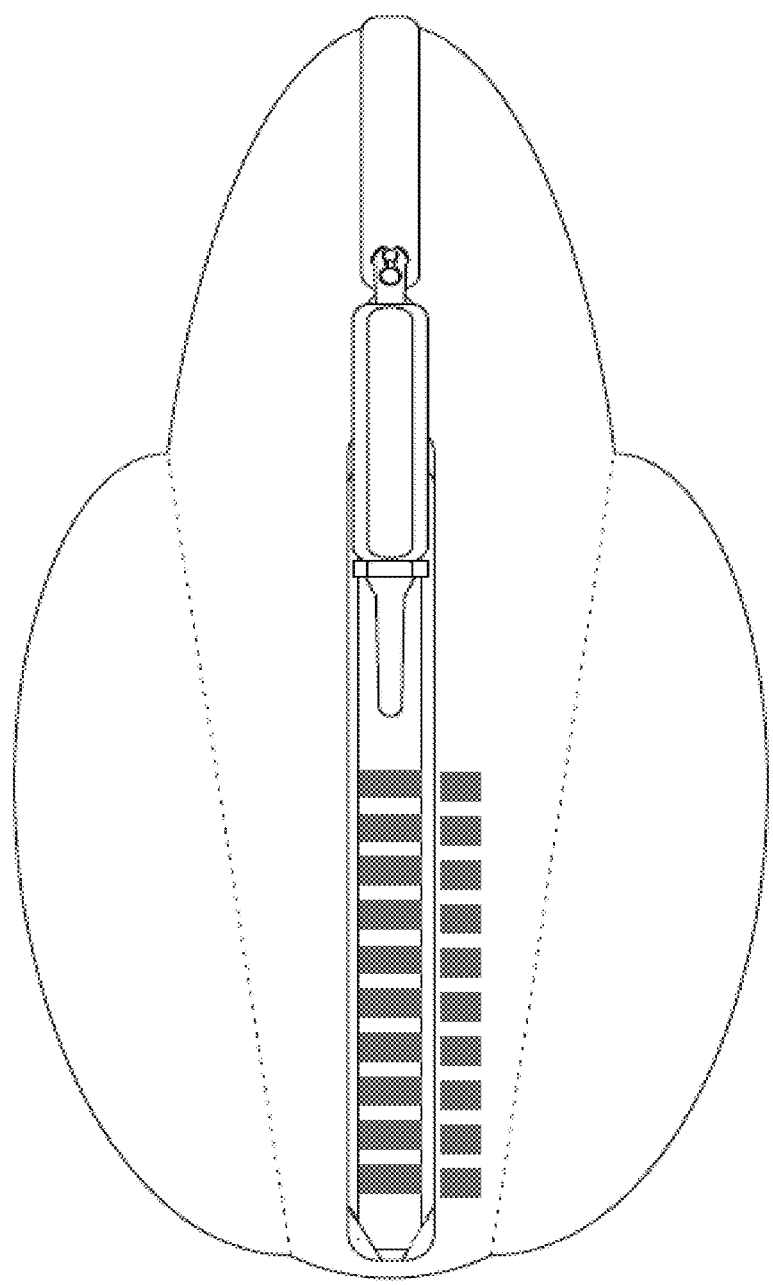
FIG. 3 is a depiction of the urine collection device attached to a strip holder.
Figures 5A, 5B:
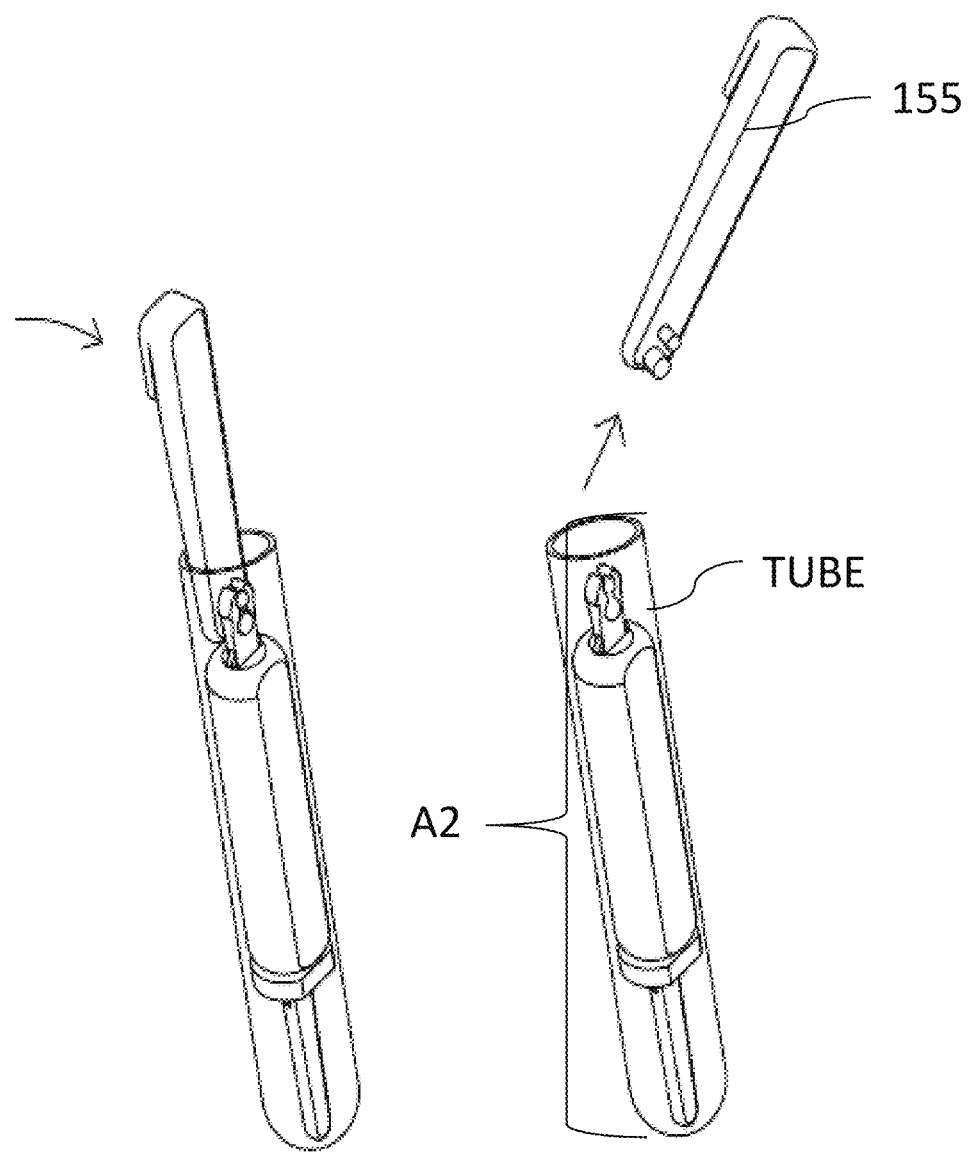
FIGS. 5A and 5B are depictions of a mechanism for removing the clip from the urine collection device.

Assembly 1 (A1) comprises collection device 195 operatively connected to clip 155. Sponge holder 110A is integrated into this variant of collection device 195, wherein sponge holder 110A receives sponge 150A. In FIG. 1, a perspective view of A1 is depicted. In FIG. 2A, a front view of A1 is depicted. In FIG. 2B, a rear view of A1 is depicted, which is a 180 degree rotation of FIG. 2A. In FIG. 2C, a side view of A1 is depicted, which is a 90 degree rotation of FIG. 2A. In FIG. 3, A1 is placed in contact with a urine analysis strip holder. Stated another way, collection device 195 may be attached to the urine analysis strip holder by clip 155. Thereby, the urine strip holder can be held together with collection device 195. The combination of the urine strip holder held together with collection device 195 can be handled by the user of collection device 195. For a user performing only urine specimen collection, the user can simply hold clip 155 and urinate on collection device 195 such that the sponge absorbs the urine. Thus, the urine strip holder is not necessary for collector device 195 to collect urine specimens. Within the urine analysis strip holder, a basic diagnostic tool for determining pathological changes in a patient's urine is placed, such as a urine test strip. The urine test strip comprises up to 10 distinct chemical pads (with reagents that change color upon physical exposure with urine collected from the sponge). Color changes may indicate the presence of ketones, proteins, acidic entities, and so forth in the urine collected from the sponge. In FIG. 4A, A1 is detached from a tube. In FIG. 4B, A1 is inserted into the tube from FIG. 4A. In FIG. 5A, a user can detach clip 155 from A1 at the indicated position on clip 155.

Assembly 2 (A2) comprises collection device 195 operatively connected to sponge 150A. Sponge holder 110A is integrated into this variant of collection device 195, whereby clip 155 has been detached from the collection device 195. Sponge holder 110A receives sponge 150A. In FIG. 5B, clip 155 has been detached to yield A2 from A1, wherein A2 remains inserted into the tube.

Figures 6A, 6B:
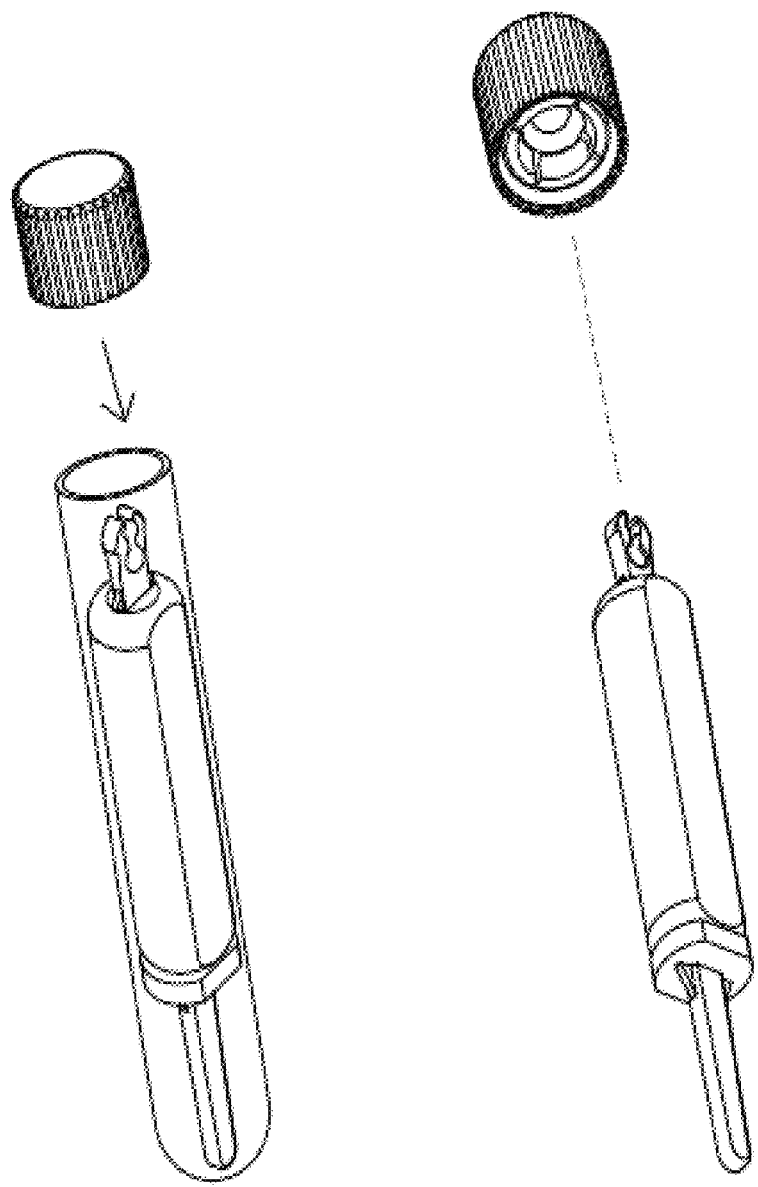
FIGS. 6A and 6B are depictions of a mechanism for connecting a cap to the urine collection device.
Figure 11:
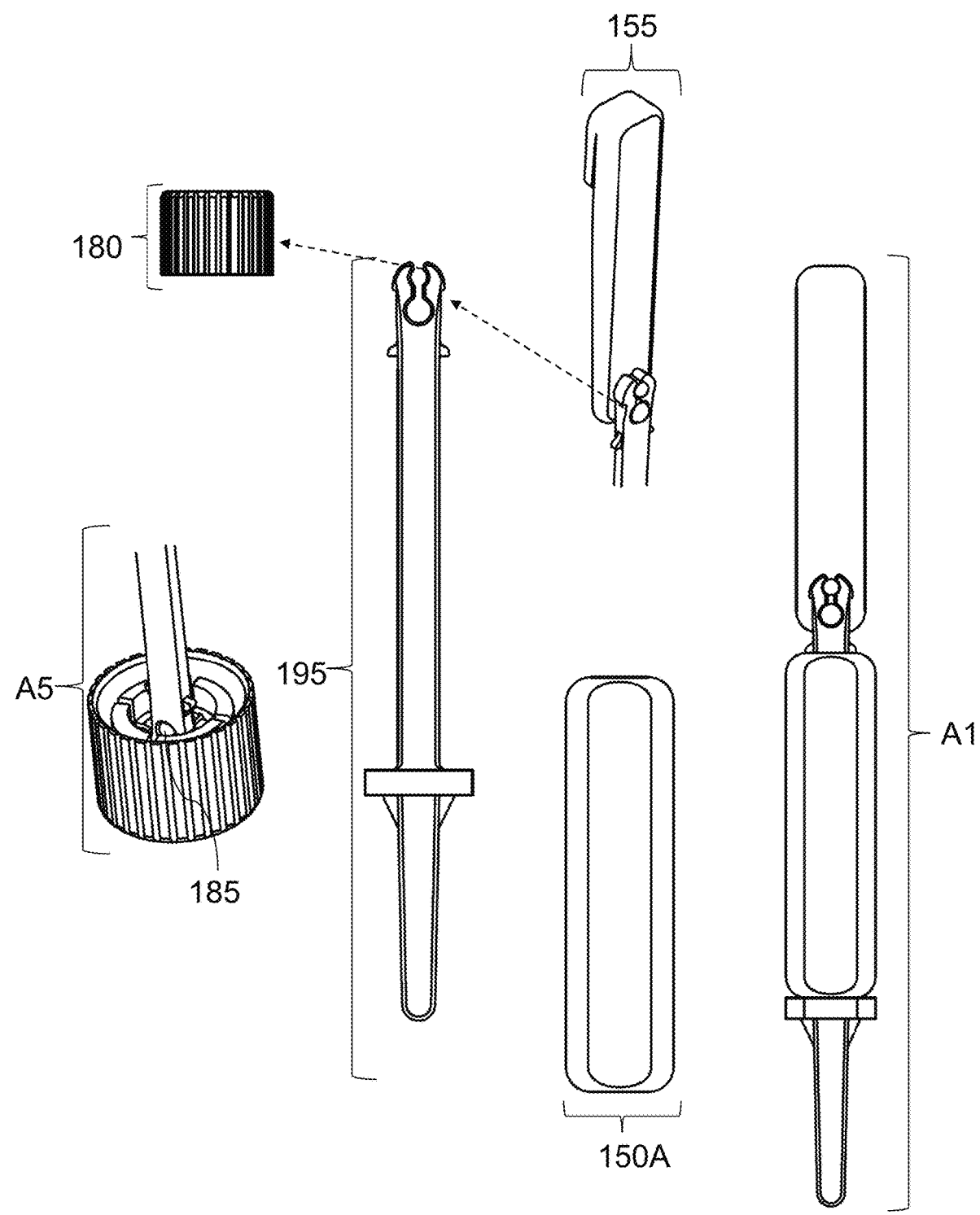
FIG. 11 is a depiction of mechanisms of attaching components to the urine collection device.

Assembly 3 (A3) comprises collection device 195 operatively connected to cap 180. Sponge holder 110A is integrated into this variant of collection device 195. Sponge holder 110A receives sponge 150A. In FIG. 6A, cap 180 comprises extender 185 (as depicted in FIG. 11) to receive collection device 195 which resides within the tube. In FIG. 6B, cap 180 comprises extender 185 (as depicted in FIG. 11)

to receive collection device 195 which is outside of the tube. In FIG. 6A and FIG. 6B, cap 180 is about to be connected to collection device 195 of A2. In FIG. 7A, cap 180 is operatively connected to the tube and collection device 195 of A2, thereby forming a capped system containing the sponge (with collected urine). In FIG. 7B, the capped system can undergo centrifuge or other processes in which collected urine in the sponge migrates to the bottom of the tube.

Assembly 4 (A4) comprises the tube where urine from a sponge (sponge 150A, 150B, or 150C) has been: (i) collected in the tube and (ii) detached from A3, as depicted in FIG. 8. The connection of collector device 195, which is holding sponge 150A, to cap 180 is sturdy. By unscrewing cap 180 from the tube, A4 results without disturbing the urine in the bottom the tube. For example, 5 mL of urine migrates to the bottom of the tube, wherein the urine has been collected in the sponge.

Figure 9:
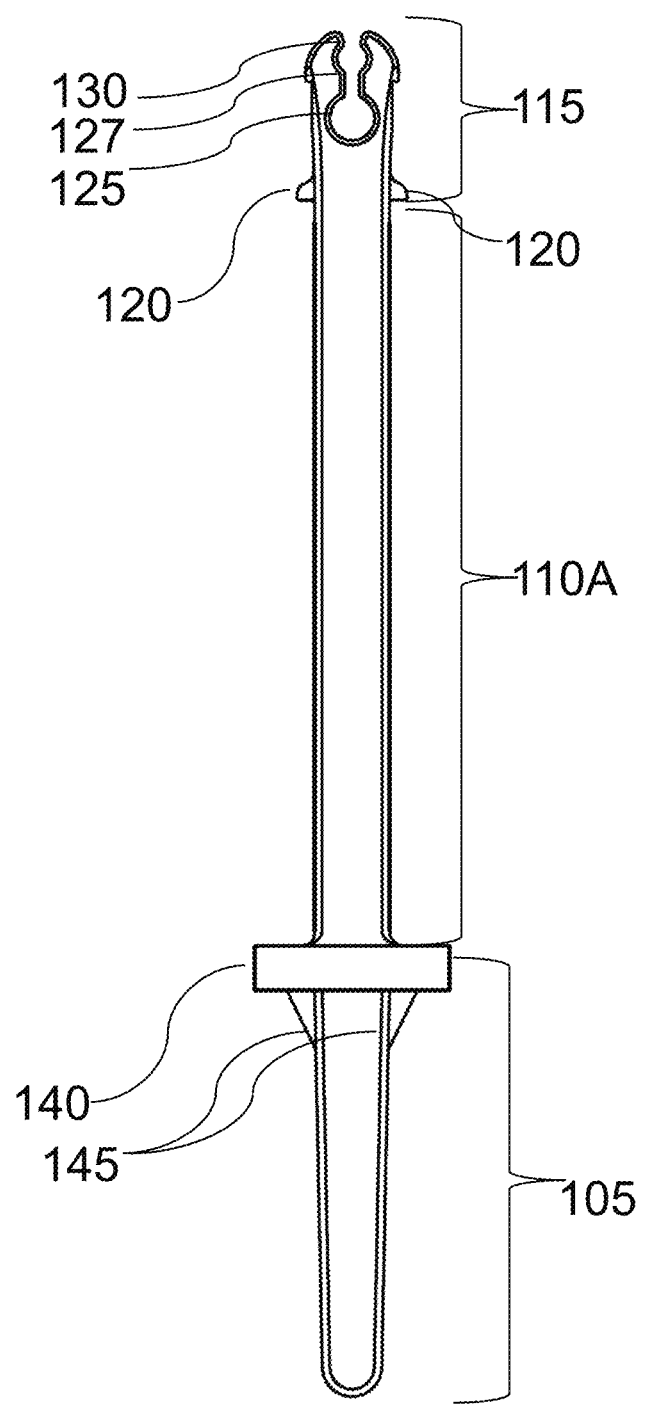
FIG. 9 is a depiction of components of the urine collection device.
Figure 10:
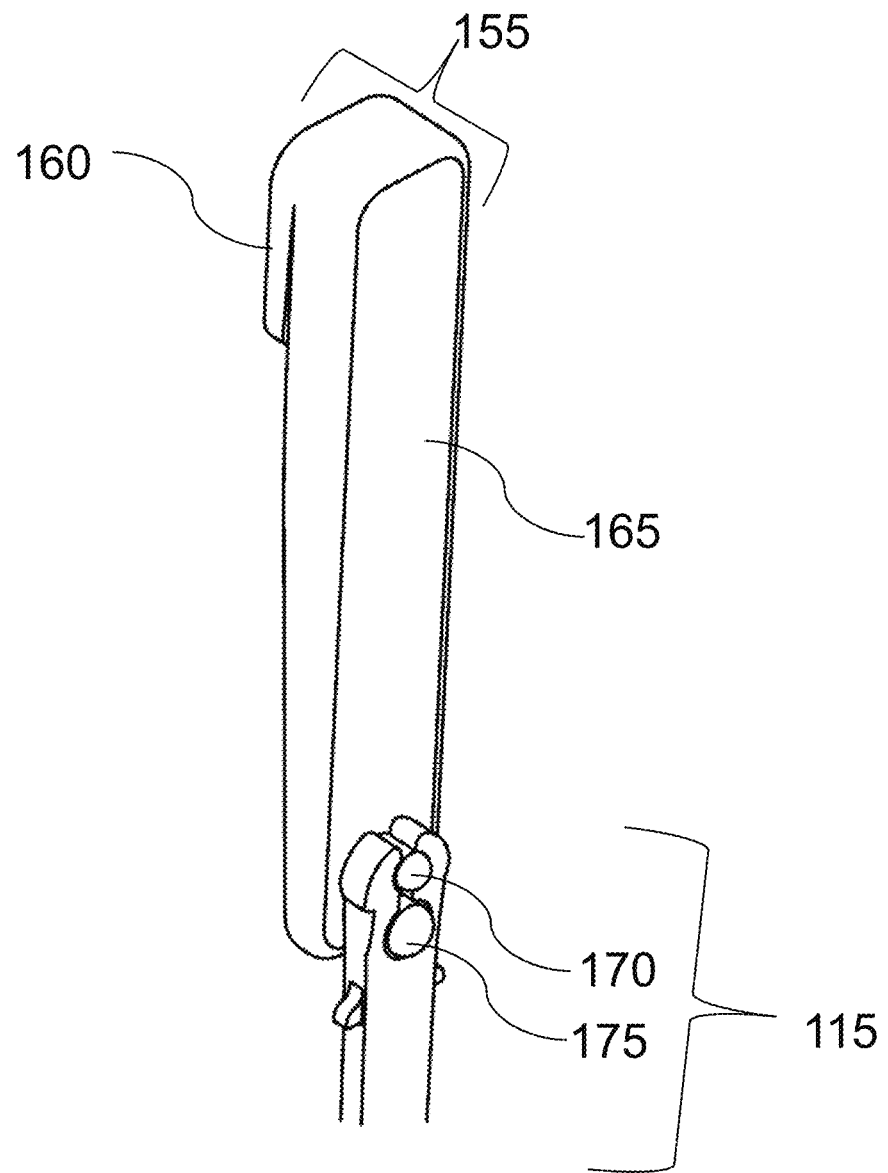
FIG. 10 is a depiction of components of the clip.
Figure 12:
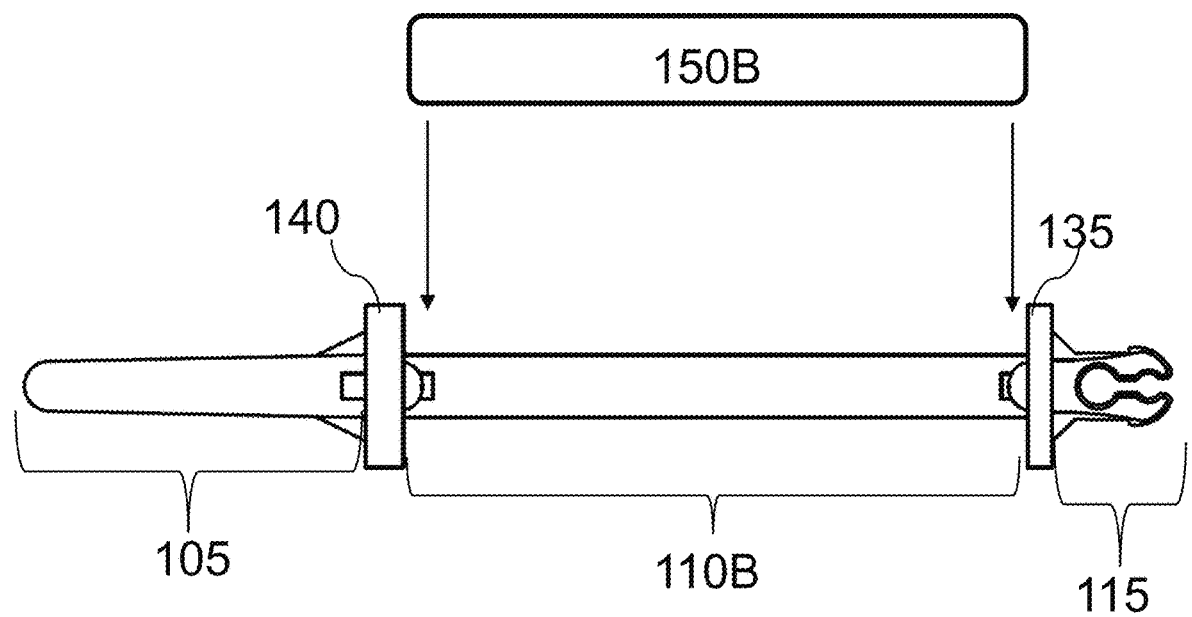
FIG. 12 is a depiction of top view of a urine collection device having a wall and a seat without knobs.
Figure 13:
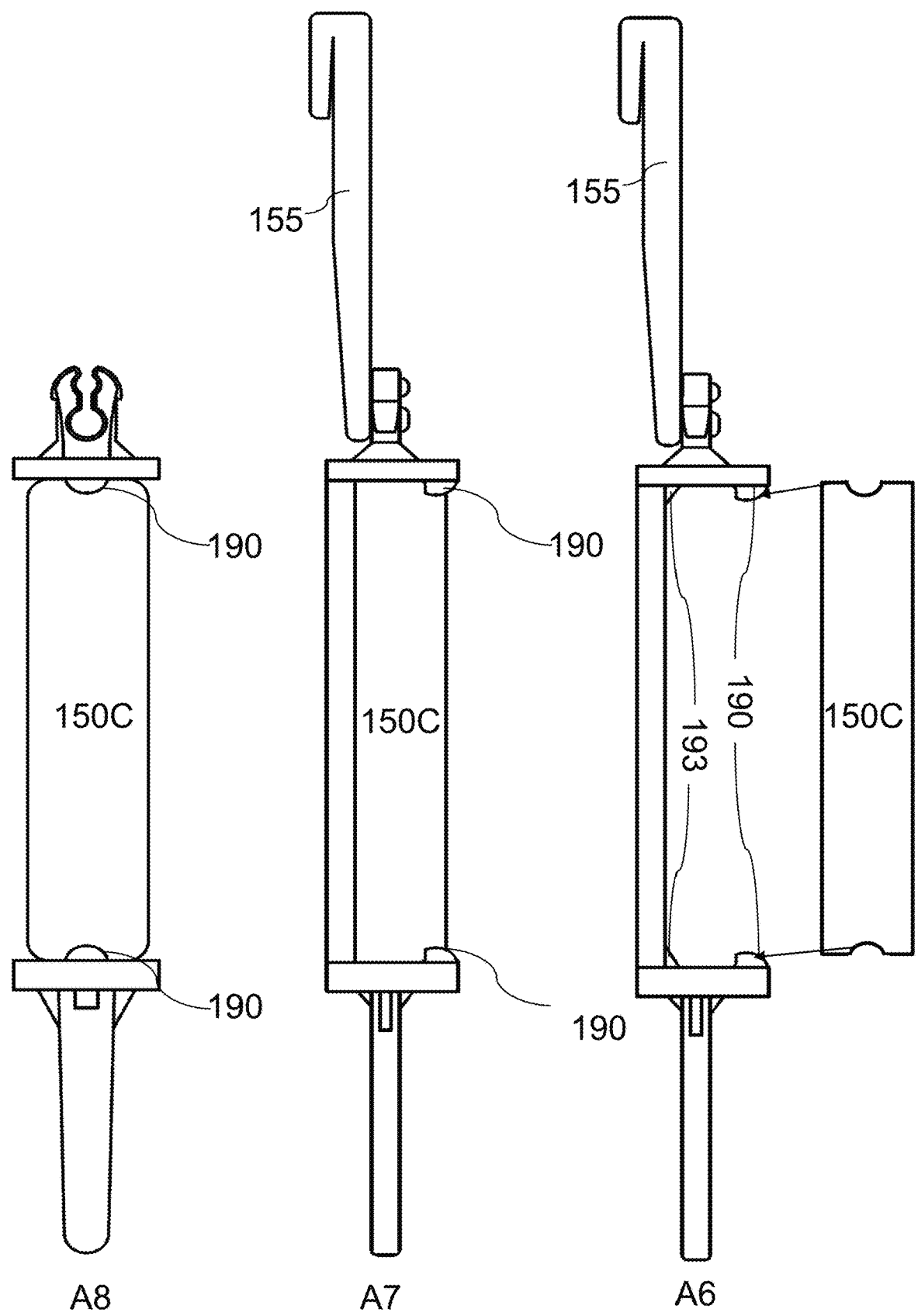
FIG. 13 is a depiction of a urine collection device having a wall and a seat with knobs.

The collector portion of sponge-mounted urine collection device (e.g. UriSponge™) is collection device 195, as depicted in FIG. 9. Collection device 195 can be attached to and detached from clip 155 at connector 115 of collection device 195, wherein connector 115 is operatively connected to sponge holder 110A or sponge holder 110B of collection device 195. Sponge holder 110A or 110B is operatively connected to sponge stopper 105 of collection device 195. Sponge stopper 105 is configured to contact a bottom surface of a tube and offset sponge holder 110A away from the bottom surface of the tube. Sponge holder 110A comprises side extenders 120 and seat 140, which are arranged such that sponge 150A (which has a concave groove) fits in between side extenders 120 and seat 140. In an embodiment, sponge holder 110B comprises wall 135 and seat 140, which are arranged such that sponge 150B fits in between wall 135 and seat 140. In another embodiment, sponge holder 110C comprises wall 135 and seat 140 such that there is at least one unit of knob 190 and rear extender 193 disposed on the surface of wall 135 and seat 140, as depicted in FIG. 13. In FIG. 12, sponge 150B is rectangular and fits within wall 135 and seat 140, which define the top and bottom boundaries of sponge holder 110B. In contrast, sponge 150C contains two grooves to fit within each unit of knob 190 and two grooves to fit with each unit of knob 193. In FIG. 13, Wall 135 and seat 140 are arranged such that sponge 150C fits in between wall 135 and seat 140, which each have a unit of knob 190 and rear extender 193 attached thereon. Rear extender 193 protrudes up and away from sponger holder 110B.

Assembly 5 (A5) comprises cap 180 operatively connected to collection device 195, as depicted in FIG. 11. Sponge holder 110A is integrated into collection device 195. Stated another way, cap 180 is configured to receive connector 115 of collection device 195.

Assembly 6 (A6) comprises collection device 195 operatively connected to clip 155. Sponge holder 110B, which comprises two units of knob 190 and two units of rear extender 193, is integrated into this variant of collection device 195, wherein sponge holder 110B is configured to receive sponge 150C, as depicted in FIG. 13.

Assembly 7 (A7) comprises collection device 195 operatively connected to clip 155 and sponge 150C. Sponge holder 110B, which comprises two units of knob 190 and two units of rear extender 193, is integrated into this variant of collection device 195, wherein sponge holder 110B receives sponge 150C, as depicted in FIG. 13.

Figure 15:
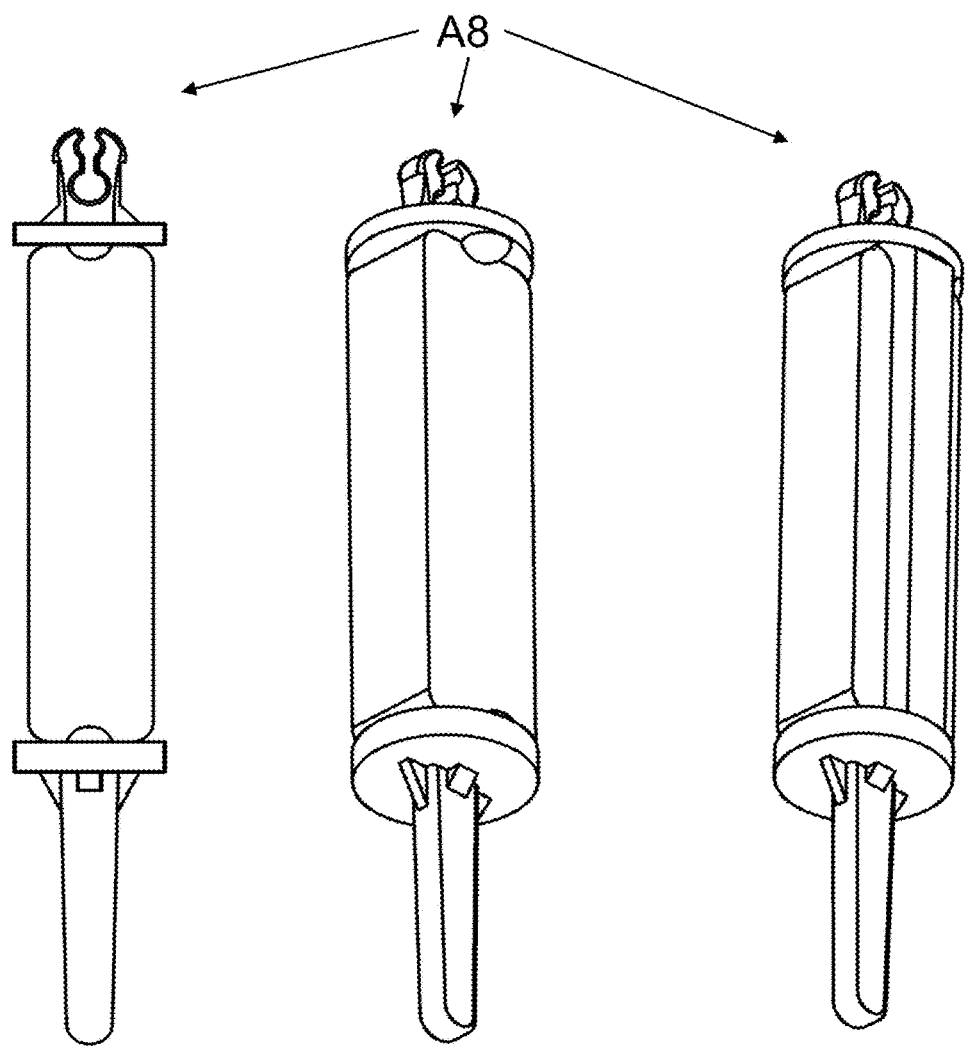
FIG. 15 is a depiction of the urine collection device having the wall and the seat with the knobs, where a sponge is disposed in between the wall and the seat and the cap is disconnected.

Assembly 8 (A8) comprises collection device 195 operatively connected to sponge 150C. Clip 155 has been detached from A7 to yield A8, as depicted in FIG. 13. Other views of A8 are depicted in FIG. 15.

Figure 14:
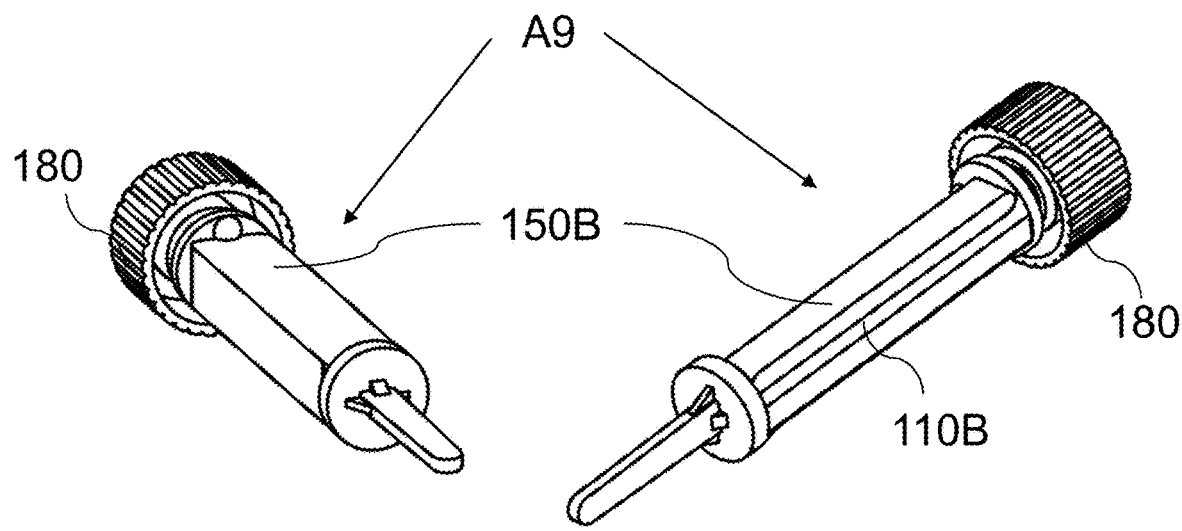
FIG. 14 is a depiction of the urine collection device having the wall and the seat with the knobs, where a sponge is disposed in between the wall and the seat and a cap is connected to the urine collection device.

Assembly 9 (A9) comprises collection device 195 operatively connected to sponge 150C and cap 180. Sponge holder 110B, which comprises two units of knob 190 and two units of rear extender 193, is integrated into this variant of collection device 195, wherein sponge holder 110B receives sponge 150C. Two different views of the A9 are depicted in FIG. 14.

Figure 16:
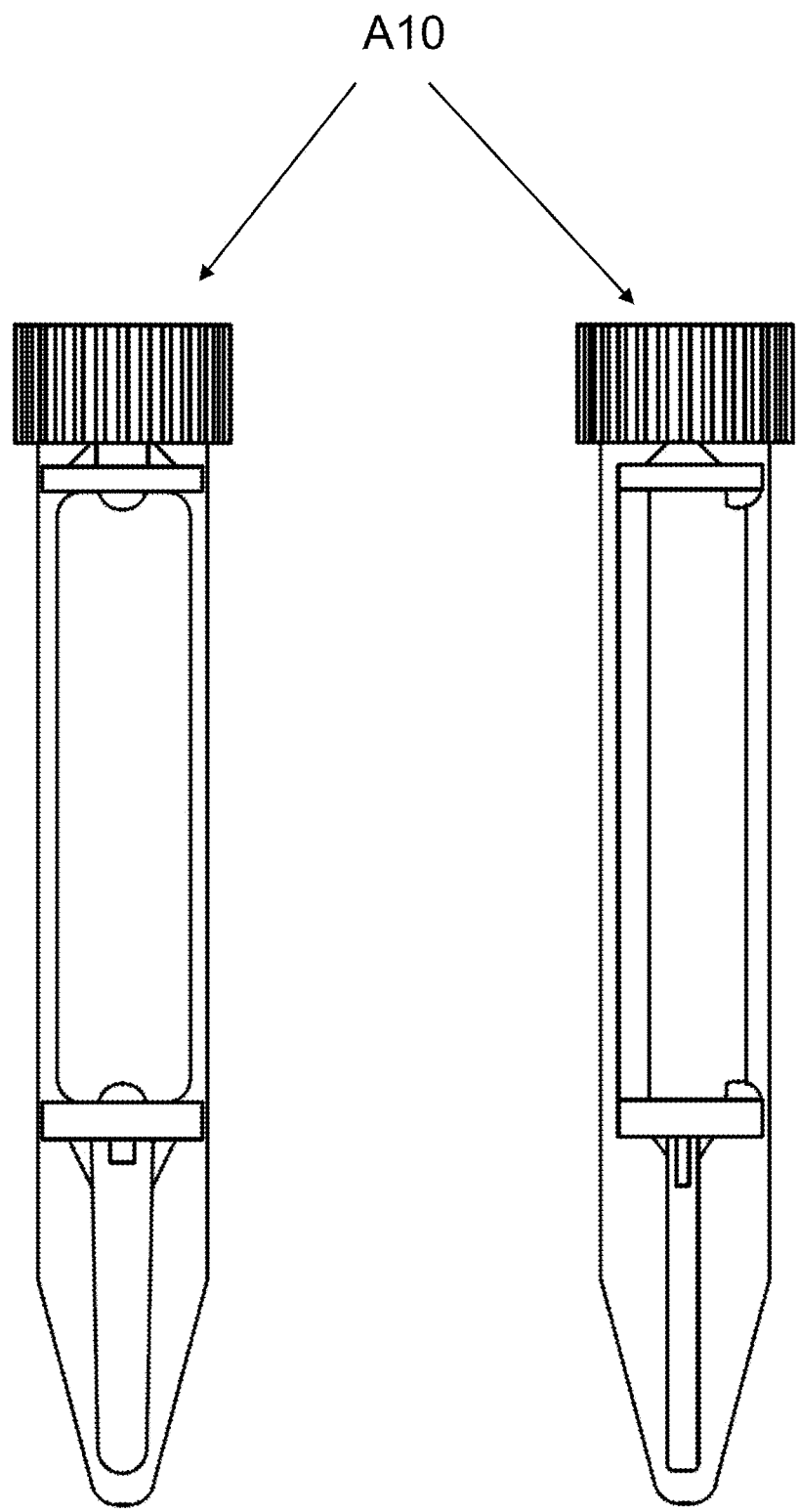
FIG. 16 is a depiction of the urine collection device having the wall and the seat with the knob, where a sponge is disposed in between the wall and the seat and the cap is connected to the urine collection device and tube for centrifuging.

Assembly 10 (A10) comprises collection device 195 operatively connected to sponge 150C, cap 180, and the tube (similar or identical to the tube described above). Sponge holder 110B, which comprises two units of knob 190 and two units of rear extender 195, is integrated into this variant of collection device 195, wherein sponge holder 110B receives sponge 150C, as depicted in FIG. 16. Cap 180 is operatively connected to collection device 195 via attachment of extender 185 of cap 180 with connector 115 of collection device 195. Connector 115 comprises receiving cavity 125, receiving cavity 127, and receiving cavity 130 to form sturdy connections with cap 185. Receiving cavity 130 and receiving cavity 127 have curve-shaped cavity regions which are connected by a straight-shaped receiving cavity 127. Clip 115 can also attach to receiving cavity 125, receiving cavity 127, and receiving cavity 130 of connector 115 to form sturdy connections and readily detach from receiving cavity 125, receiving cavity 127, and receiving cavity 130 of connector 115. The sturdy connections between connector 115 and clip 155 are formed upon receiving extender 170 operatively connecting to receiving cavity 130 and receiving extender 175 operatively connecting to receiving cavity 125. Clip 155 comprises base 165 and base 160, wherein base 165 and base 160 are fused together. Receiving extenders 170 and 175 are disposed on the bottom portion of base 165. Base 160 is disposed on the top portion of base 165. Base 160 protrudes outwards, whereby the user can apply a force against base 160 to detach clip 155 from A1, as depicted in FIG. 5A and FIG. 5B.

Figure 17A:
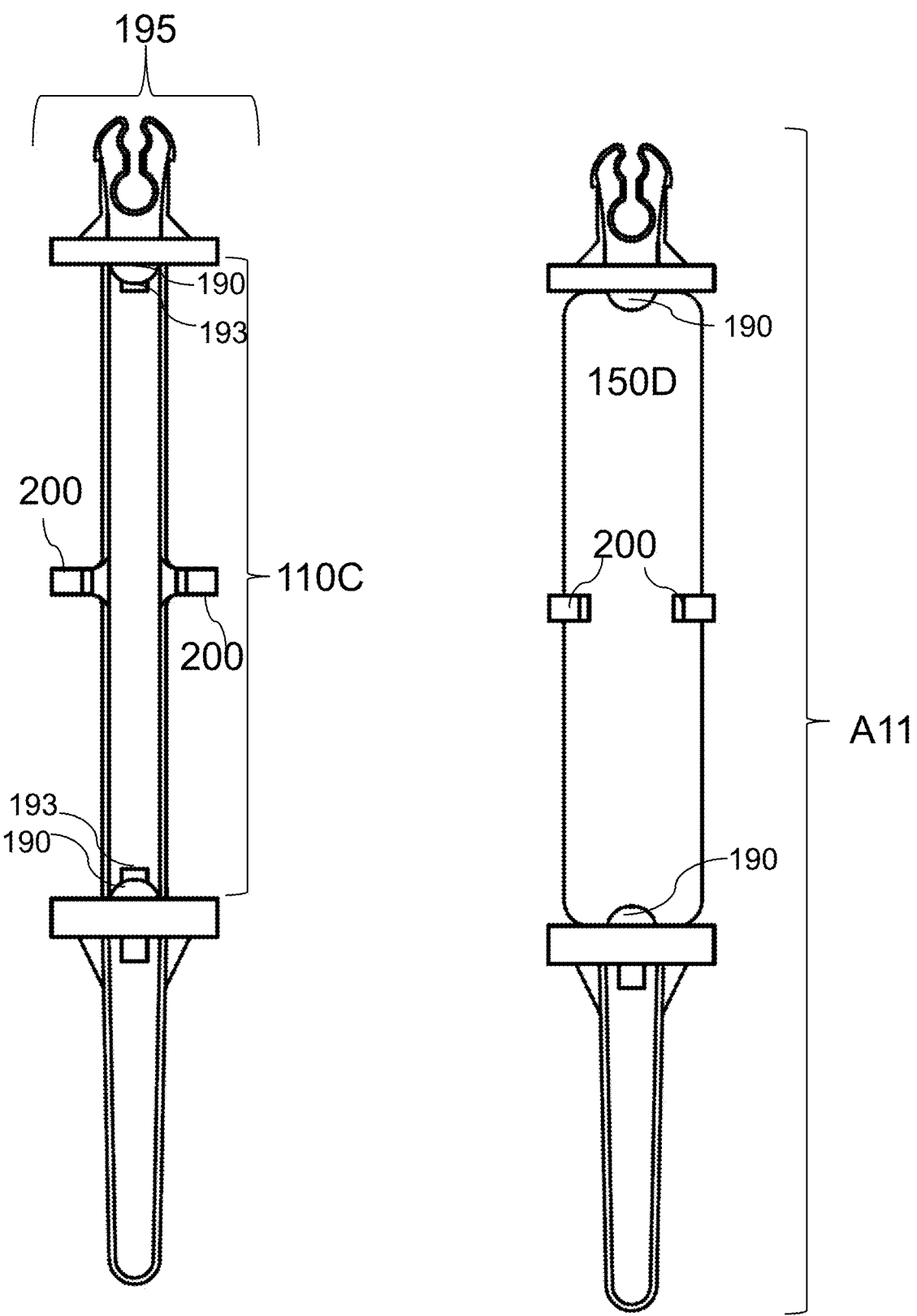
FIG. 17 is a depiction of the urine collection device having the wall and the seat with knobs and clips, where a sponge is disposed in between the wall and the seat and the cap is connected to the urine collection device and tube for centrifuging.
Figure 17B:
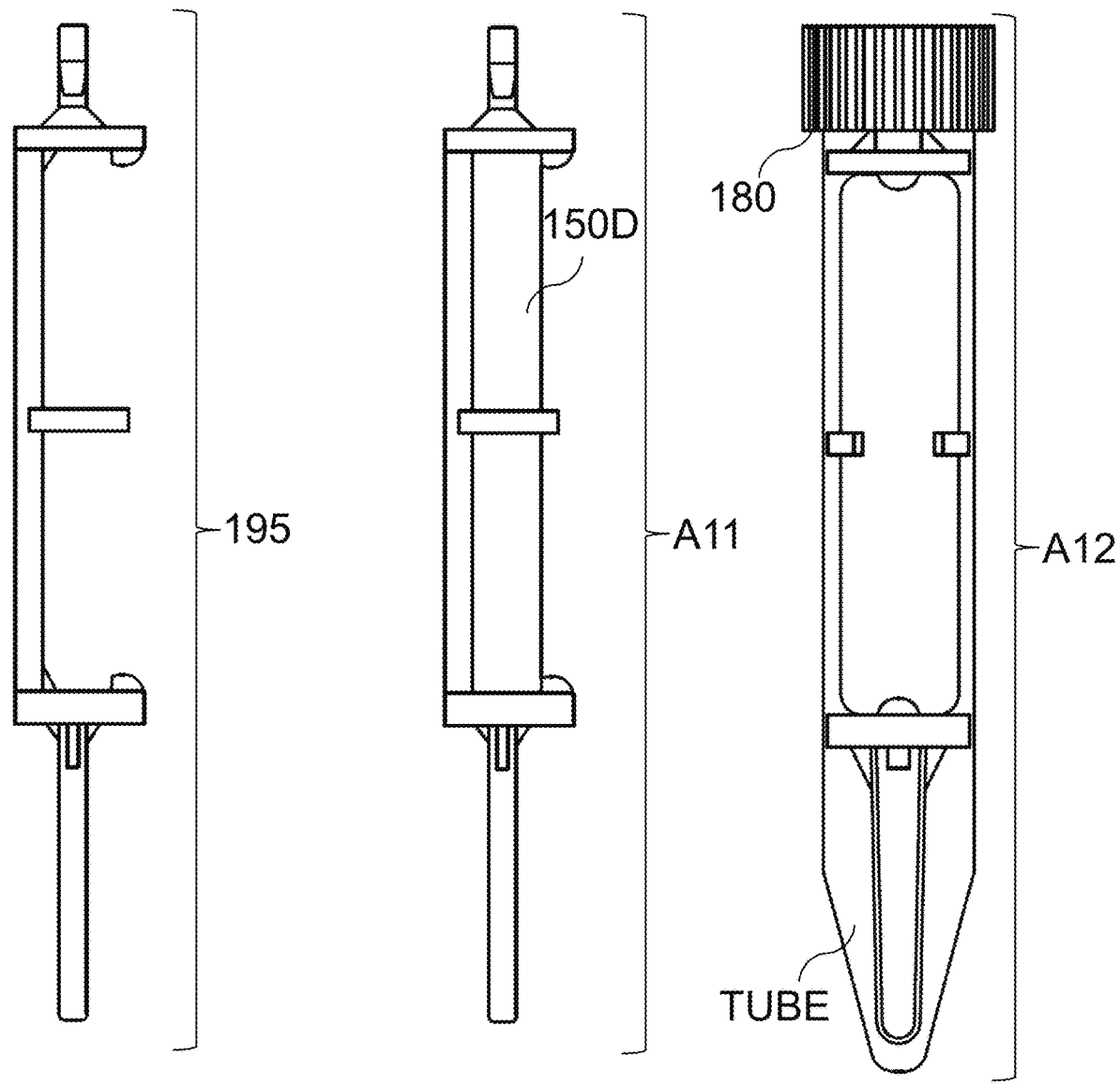
Figure 18:
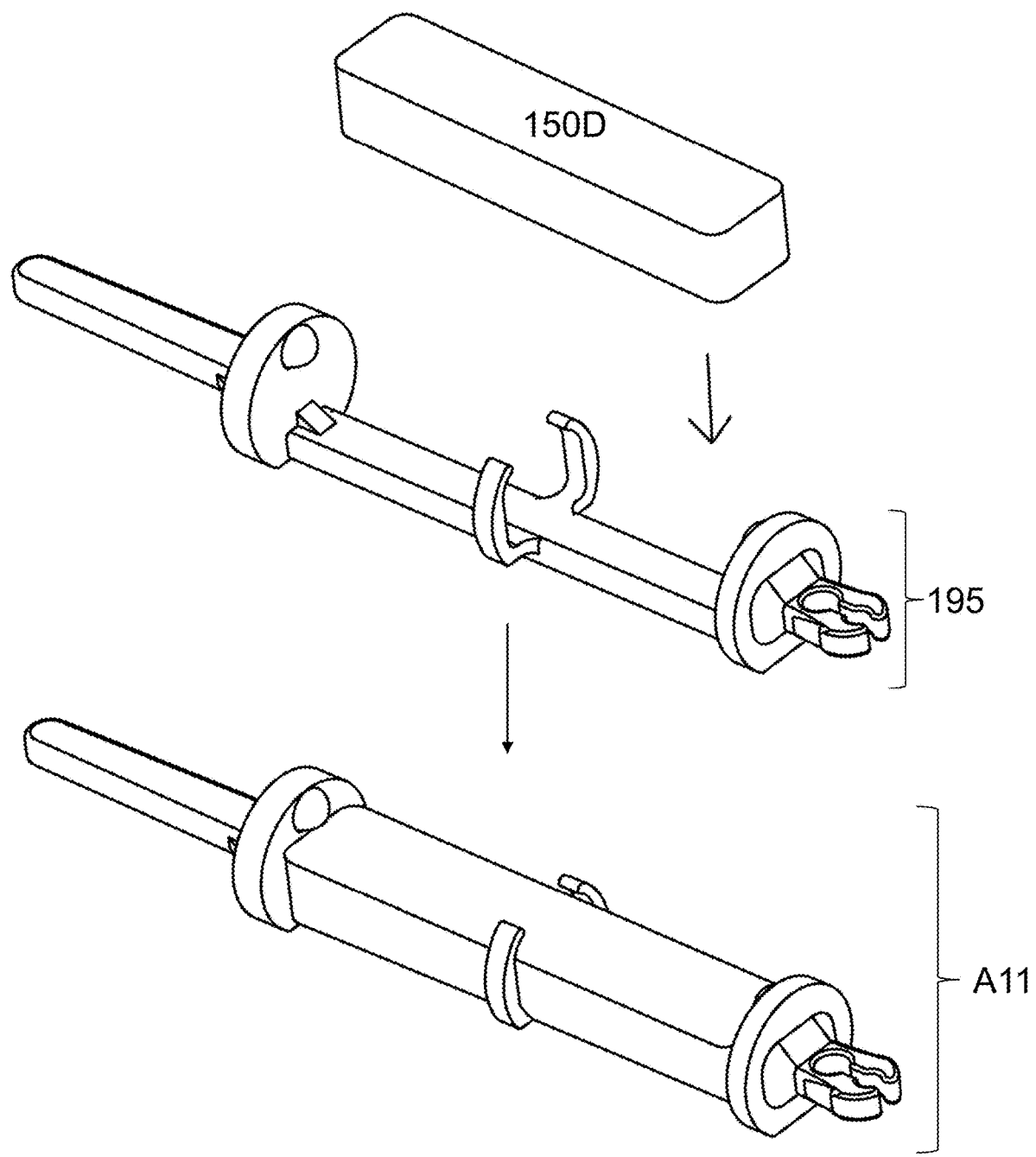
FIG. 18 is a depiction of a mechanism of attaching the sponge to the urine collection device having the wall and the seat with knobs and clips.

Assembly 11 (A11) comprises collection device 195 operatively connected to sponge 150D, as depicted in FIG. 17A, FIG. 17B, and FIG. 18. Sponge 150D comprises straight line incisions in the body of the sponge, as depicted in FIG. 18. Sponge holder 110C, which comprises two units of knob 190, two units of rear extender 193, and two units of clips 200, is integrated into this variant of collection device 195, wherein sponge holder 110C receives sponge 150D, as depicted in FIG. 17A, FIG. 17B, and FIG. 18. Sponge 150D makes a supple fit within the two units of knob 190 and the two units of clip 200 such that the straight line incisions of sponge 150D attach to the two units of clip 200.

Assembly 12 (A12) comprises collection device 195 operatively connected to sponge 150D, cap 180, and the tube. The tube also connects to cap 180, wherein cap 180 attaches to connector 115 of collection device 195. Sponge holder 110C, which comprises two units of knob 190, two units of rear extender 193, and two units of clips 200, is integrated into this variant of collection device 195, wherein sponge holder 110C receives sponge 150D, as depicted in FIG. 17.

Figure 19:
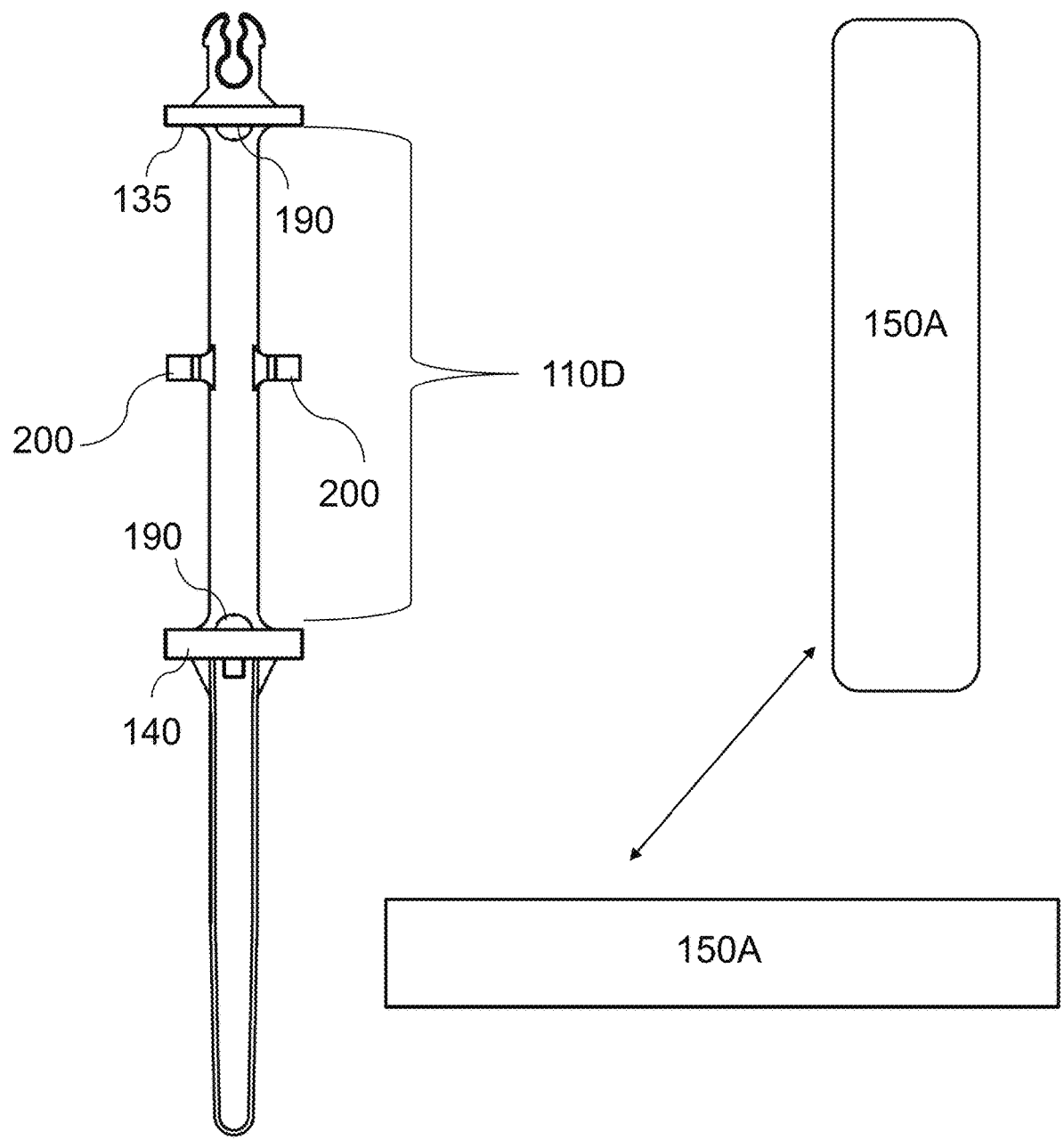
FIG. 19 is a depiction of a collection device and sponge.
Figure 20:
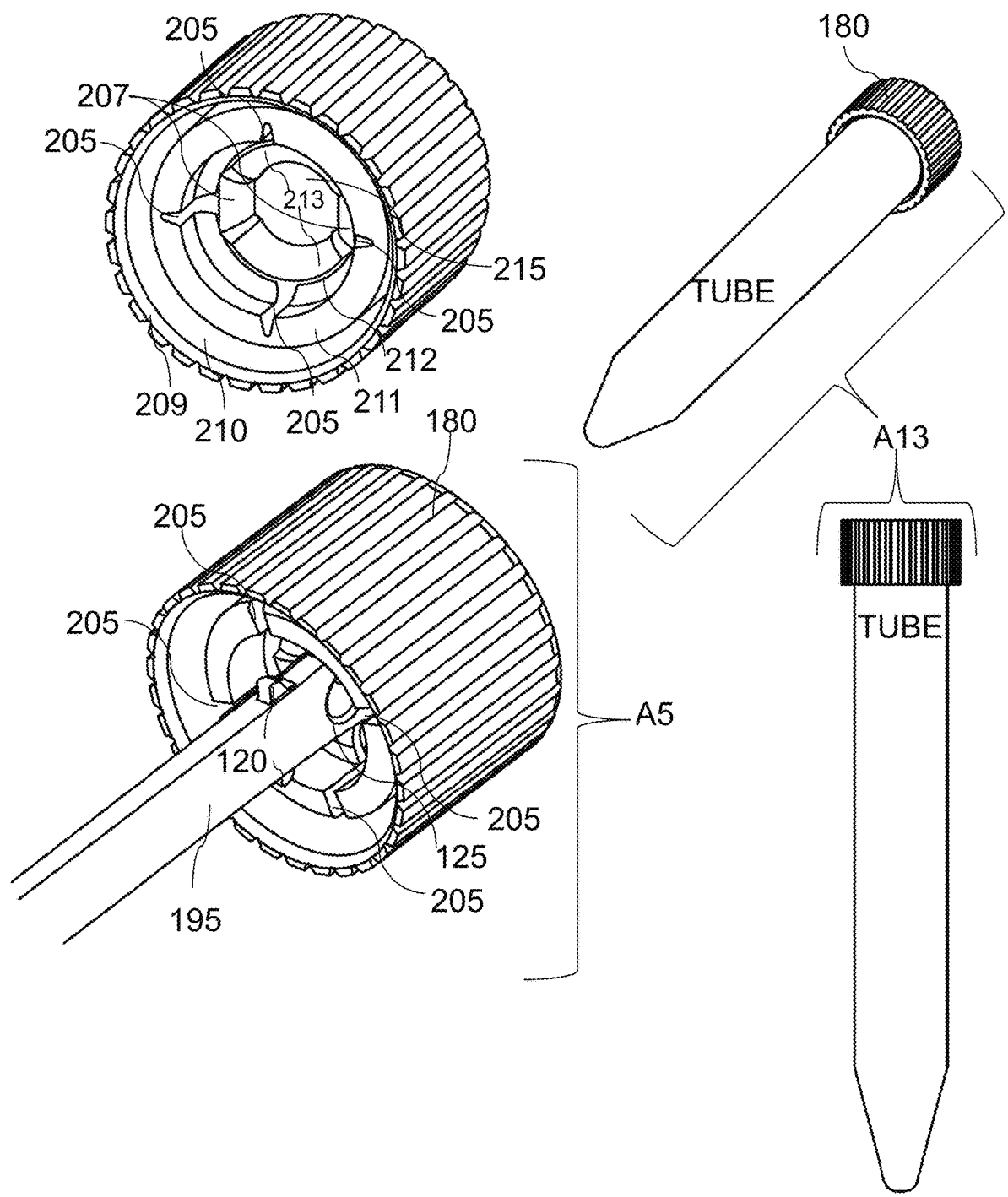
FIG. 20 is a depiction of the dimensions of a cap and tube.

As depicted in FIG. 19, collection device 195 comprises sponge holder 110D. A unit of knob 190 is disposed on seat 140 and a unit of knob 190 is disposed on wall 135. Two units of clip 200 are disposed on the sides of sponge holder 110D. Sponge 150A is contained within the two units of knob 190 and the units of clip 200, a disposed onto sponge holder 110D. The length of sponge holder 110D is 51.80 cm, the length spanning from sponge stopper 105 to wall 135 is 103.80 cm, the length spanning from sponge stopper 105 to seat 140 is 47.00 cm, and the length spanning from sponge stopper 105 to connector 115 is 112.79 cm. As depicted in FIG. 20, the dimensions of sponge 150A are 11.26 cm by 51.80 cm by 8.24 cm.

Assembly 13 (A13) comprises cap 180 and the tube (similar to the ones above), as depicted in FIG. 20. Cap 180 may be screwed on or pressed onto the top portion of the tube to make sturdy fit. Cap 180 comprises layers 209, 210, 211, and 212. The ridges on cap 180 are disposed on layer 209, which is operatively connected to layer 210. Layer 210 is disposed in between layer 209 and layer 211. Layer 211 is disposed in between layer 210 and layer 212. Layer 212 is disposed in between layer 211 and layer 213. Layer 213 comprises two parts which are arranged such that two units of groove 207 reside within the two parts of layer 213 such that the two units of groove 207 are opposite to each other and cavity 215 separates the two parts of layer 213. There are four units of groove 205 spanning layers 211 and 212. The entirety of layer 211 is spanned by each unit of groove 205, whereas groove 205 spans a portion of layer 212. Two of the four units of groove 205 are operatively connected to groove 207. Two units of groove 205 are operatively connected to layer 213. As depicted in A5 in FIG. 20, cavity 125 aligns with the two units of groove 205 operatively connected to layer 213 and side extenders 120 can be received by the by the two units of groove 205 operatively connected to layer 213.

What is claimed is:

1. A kit for urine collection, comprising:
    a clip;
    a collector device comprising a connector portion configured for receiving the clip to removably join the clip to the collector device, a holder portion configured for receiving a sponge, and a stopper portion;
    a tube configured to receive the collector device; and
    a cap configured to be inserted onto an open end of the tube and seal the tube and simultaneously receive the connector portion of the collector device into a recess disposed inside the cap to join the cap to the collector device;
    wherein the clip is configured to be held by a user when joined to the collector device, while the user urinates on the collector device;
    wherein the cap is configured to receive the connector portion of the collector device when the clip is not joined to the connector portion.

2. The kit of claim 1, further comprising a foil packet, wherein the foil packet comprises an air tight seal, a top portion configured for tearing, and material for resisting temperature changes, thereby protecting contents within the foil packet, wherein the contents comprise the clip, the collector device, the tube, and the cap.

3. A collector device, comprising:
    a connector portion configured for receiving a clip to removably join the clip to the collector device, the clip being configured to be held by a user when joined to the collector device, while the user urinates on the collector device;
    a holder portion configured for receiving a sponge, wherein the holder comprises a back wall, a seat, a wall, a first knob extending from a lip of the seat toward the wall, and a second knob extending from a lip of the wall toward the seat, the back wall extending between the seat and the wall, such that the sponge is disposed in between the seat and the wall and is propped against the back wall by the first knob and the second knob;
    a stopper portion configured to contact a bottom surface of a tube; and
    a cap, wherein the cap is configured to seal the tube when the clip is not joined to the connector portion.

4. The collector device of claim 3, wherein:
    the connector comprises a first cavity and a second cavity configured to cooperate with the clip; and
    the first cavity is operatively connected to the second cavity via a third cavity.

5. The collector device of claim 4, wherein the first cavity and the second cavity are receiving cavities and the third cavity is a pathway between the first cavity and the second cavity.

6. The collector device of claim 3, wherein when the tube is spun in a centrifuge, urine is collected at the bottom surface of the tube.

7. A collector device, comprising:
    a connector portion configured for receiving a clip to removably join the clip to the collector device, the clip being configured to be held by a user when joined to the collector device, while the user urinates on the collector device;
    a holder portion configured for receiving a sponge, wherein the holder comprises a seat and a plurality of extenders, thereby the sponge is disposed in between the seat and the plurality of extenders;
    a stopper portion configured to contact a bottom surface of a tube and offset the holder portion away from the bottom of the tube; and
    a cap, wherein the cap is configured to seal the tube when the clip is not joined to the connector portion.

8. The collector device of claim 7, wherein:
    wherein the connector comprises a first cavity and a second cavity;
    the first cavity is operatively connected to the second cavity via a third cavity.

9. The collector device of claim 8, wherein the first cavity and the second cavity are receiving cavities and the third cavity is a pathway between the first cavity and the second cavity.

10. The collector device of claim 7, wherein when the tube is spun in a centrifuge, urine is collected at the bottom surface of the tube.

11. The collector device of claim 7, wherein the cap comprises a groove configured to receive an end of the connector when the clip is not joined to the connector, wherein when the device is placed in the tube, and the cap is sealed onto the tube, the connector is received into the groove of the cap into an assembly whereby the device may be removed from the tube by handling only the cap.

12. The collector device of claim 3, comprising pronged clip,
    extending from the back wall parallel to the wall and the seat, the pronged clips being configured to hold the sponge against the back wall.

* * * * *